United States Patent [19]

Crisp et al.

[11] Patent Number: 4,817,651

[45] Date of Patent: Apr. 4, 1989

[54] HAND AND FOREARM CLEANSING APPARATUS

[75] Inventors: William E. Crisp, Phoenix; Richard C. Kudlicki; Judson L. Smith, both of Tempe, all of Ariz.

[73] Assignee: Scientific Growth, Inc., Tempe, Ariz.

[21] Appl. No.: 112,299

[22] Filed: Oct. 26, 1987

[51] Int. Cl.[4] .............................................. B08B 3/02
[52] U.S. Cl. ...................................... 134/102; 134/181; 134/182; 134/199; 134/201; 128/366; 604/289; 239/750
[58] Field of Search ............... 134/102, 179, 180, 181, 134/182, 199, 201; 422/28, 292; 4/619, 620; 128/366; 239/242, 750, 264; 604/289; 15/210; 132/74.5

[56] References Cited

U.S. PATENT DOCUMENTS

| | | | |
|---|---|---|---|
| 2,386,455 | 10/1945 | Green | 239/264 X |
| 2,769,547 | 11/1956 | Hirsch | 239/750 X |
| 2,826,763 | 3/1958 | Bass | 4/158 |
| 3,081,471 | 3/1963 | Newell | 15/210 |
| 3,757,806 | 9/1973 | Baaskar et al. | 134/199 X |
| 3,844,278 | 10/1974 | Weider . | |
| 3,918,987 | 11/1975 | Kopfer | 134/199 X |
| 4,020,856 | 5/1977 | Masterson | 132/74.5 |
| 4,219,367 | 8/1980 | Cary, Jr. et al. | 134/199 X |
| 4,402,331 | 9/1983 | Taldo et al. | 134/199 X |
| 4,496,519 | 1/1985 | McGuire | 239/750 X |
| 4,670,010 | 6/1987 | Dragone | 422/292 |

Primary Examiner—Frankie L. Stinson
Attorney, Agent, or Firm—Cahill, Sutton & Thomas

[57] ABSTRACT

Cleansing apparatus comprising a pair of rotating cylinders with spray nozzles in the walls thereof. The cylinders provide cylindrical cleansing chambers which have their axes displaced from each other at an angle of approximately 30 degrees to comfortably receive the hands and forearms of a user. Certain of the nozzles in each cylinder are disposed in a helical array to sweep the forearm of the user with cleansing fluid as the cylinder is rotated. Each cylinder preferably has an inner liner and an outer liner with space there between providing a passageway for cleansing fluid to the nozzles which are preferably formed in the inner liner. An elastomeric support for each cylinder is provided. A blower may be associated with the cylinders for drawing air into the cylinders to reduce external splashing of cleansing fluid.

22 Claims, 3 Drawing Sheets

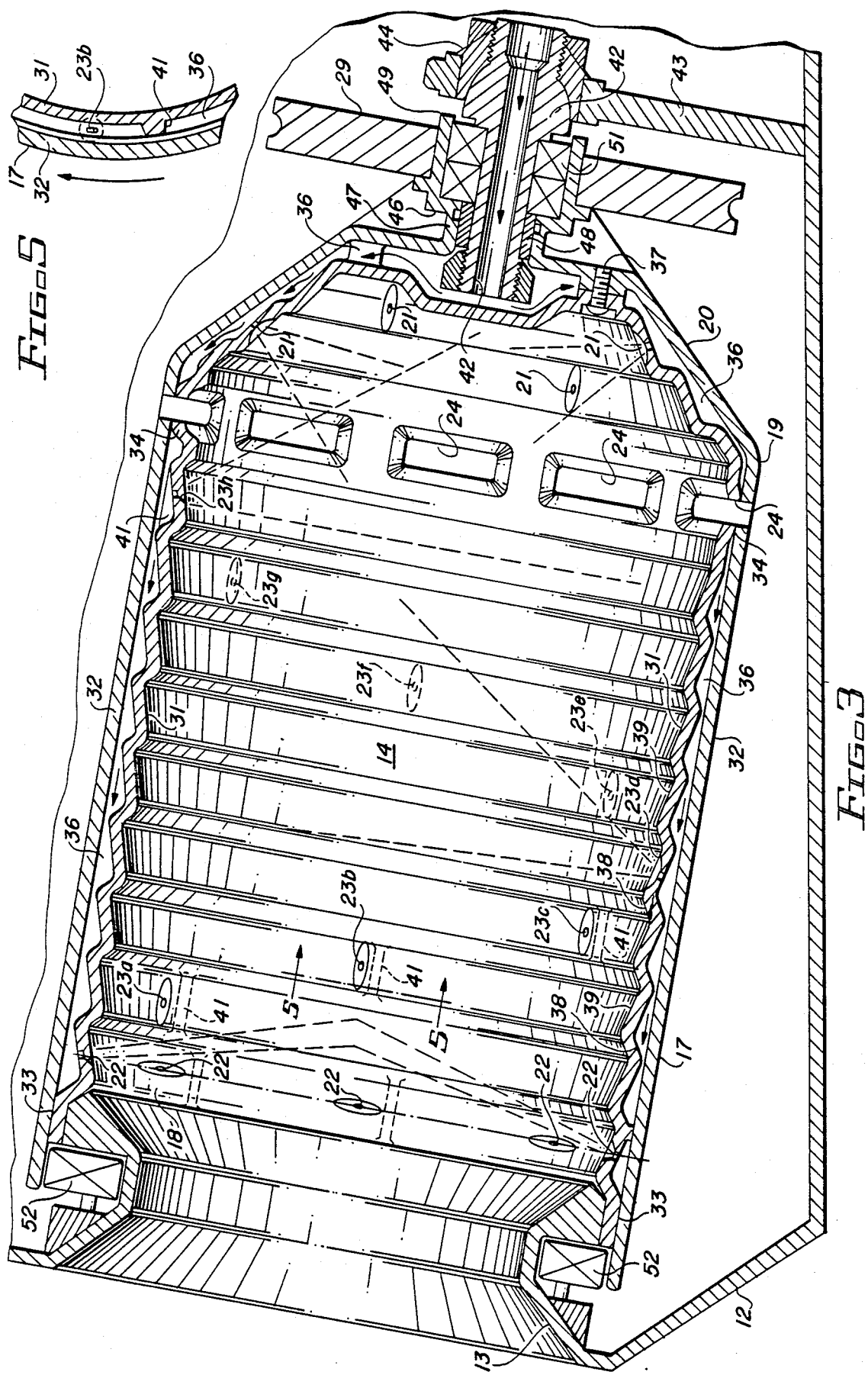

HAND AND FOREARM CLEANSING APPARATUS

TECHNICAL FIELD

This invention is concerned with cleansing the hands and forearms of persons who work in clean and even sterile environments.

BACKGROUND ART

The importance of cleanliness in the health-care field has long been recognized. The practice of pre-surgical scrubbing by surgeons and other operating room personnel is probably the epitome of efforts to cleanse the hands and forearms of persons working in sterile environments. Because of the time and effort consumed in pre-surgical scrubbing, it is not surprising that various forms of apparatus have been devised in the past to assist in the cleansing operation.

And it has been recognized that, if economical apparatus could be devised to effectively cleanse the hands and forearms of surgeons, that apparatus likely would find use in other environments as well. For example, in the electronics and aerospace industries cleanliness of the workers is essential to the fabrication of contamination-free, reliable components. In restaurants and other establishments where food is handled or prepared, cleanliness of the food handlers is of utmost importance.

The provision of apparatus by which all such personnel could quickly, easily and effectively cleanse their hands and forearms would not only provide the means for achieving the desired cleanliness but could actually encourage and induce the personnel to practice cleanliness. People are simply more likely to use the apparatus if it reduces the effort required to achieve the desired degree of cleanliness.

Some of the past attempts to provide cleansing of the character described are represented by the apparatus disclosed in the following U.S. Pat. Nos. 3,757,806, granted Sept. 11, 1973 to S. N. Bhaskar, et al for "Pulsating Hydrojet Lavage Device"; 3,918,987, granted Nov. 11, 1975 to R. J. Kopfer for "Surgeon Hand and Arm Scrubbing Apparatus"; and U.S. Pat. No. 4,402,331, granted Sept. 6, 1983 to T. J. Taldo, et al for "Portable Lavage Device".

The apparatus in all three of the aforementioned patents include chambers into which the user inserts his hands and forearms so that they may be subjected to streams of cleansing fluid from spray nozzles surrounding the chamber. A motor driven pump propels the cleansing fluid, which may be a mixture of water and soap or disinfectant, to the nozzles. In every instance the nozzles for these apparatus are stationary.

The apparatus of the Bhasker, et al and Taldo patents, subject the hands and forearms to pulsating jets of cleansing fluid. In theory, the compression-decompression effect or, so called, "trampoline" effect, on the skin is particularly effective in removing dirt and bacteria from the follicles and skin folds. However, the requirement for a heavy motor and pump to produce the pulsating jets of cleansing fluid causes the apparatus of these patents to be quite expensive. Such units also are quite noisy.

The idea of employing moving spray nozzles to treat all or some portion of the human anatomy has been advocated by some past inventors. For example, in the apparatus disclosed in U.S. Pat. No. 3,844,278, granted Oct. 29, 1974 to B. Weider for "Hydrotherapeutic Massage Device" a frusto-conical basket of nozzles is adapted to subject a human breast to a hydrotherapeutic massage. In the apparatus disclosed in U.S. Pat. No. 2,826,763, granted Mar. 18, 1958 to L. Bass for "Spray Bathing Apparatus With Scrubbers" the human body from the neck down is subjected to a washing spray from two rows of nozzles which orbit the body. Neither of these two patents contains any suggestion or indication that the apparatus therein disclosed could be adapted to cleanse just the hands and forearms of a person. Nor do they suggest that the apparatus there disclosed is capable of producing the degree of cleanliness required, for example, for pre-surgical scrubbings.

There continues to be a need for economical, but effective, apparatus for cleansing the hands and forearms of a user. Apparatus which is of sufficiently low cost to be affordably installed in a restaurant would be considered to be economical. Apparatus capable of cleansing the hands and forearms of a surgeon prior to surgery would certainly be considered to be effective.

DISCLOSURE OF THE INVENTION

The principal feature of this invention is the utilization of rotating cylinders to provide cleansing chambers. These cylinders have cleansing fluid spray nozzles in the walls thereof. These nozzles present a moving series of cleansing fluid sprays onto the hands and forearms of the user when the cylinders in which they are carried are rotated.

The nozzles in the wall of each cylinder are so constructed that they present no significant protuberances on the inner surfaces of the cylinders. In other words, the inner surface of each cylinder is smooth or at least smoothly undulating so as to present no hazard to the hands and forearms of the user when the cylinder is rotated.

A series of the nozzles in the wall of each cylinder are arranged in a helical array along the cylinder. This arrangement has the effect of sweeping the forearm and hand with a series of sprays as the cylinder is rotated. The disposition of the nozzle array and the direction of rotation of the cylinder are preferably coordinated so that the series of sprays moves down the forearm toward the hand with each revolution of the cylinder.

A further feature of the invention which is deemed to be important is that the axis of the cylindrical cleansing chambers provided by the rotatable cylinders are displaced from each other at an angle to comfortably receive the hands and the forearms of the user. With the openings to the chambers somewhat farther apart than the hand receiving portions of the chambers, when the hands and forearms are inserted into the chambers for cleansing the hands of the user will be closer together than are the elbows of the user. This is a natural and comfortable position for these extremities.

BRIEF DESCRIPTION OF THE DRAWINGS

The invention is described in greater detail hereinafter by reference to the accompanying drawings wherein:

FIG. 3 is an enlarged vertical sectional view through one of the cylinders illustrated in FIG. 2;

FIG. 5 is a fragmentary sectional view through the wall of one of the cylinders, which view is taken generally as indicated by line 5—5 in FIG. 3.

BEST MODE FOR CARRYING OUT THE INVENTION

Figure 1:
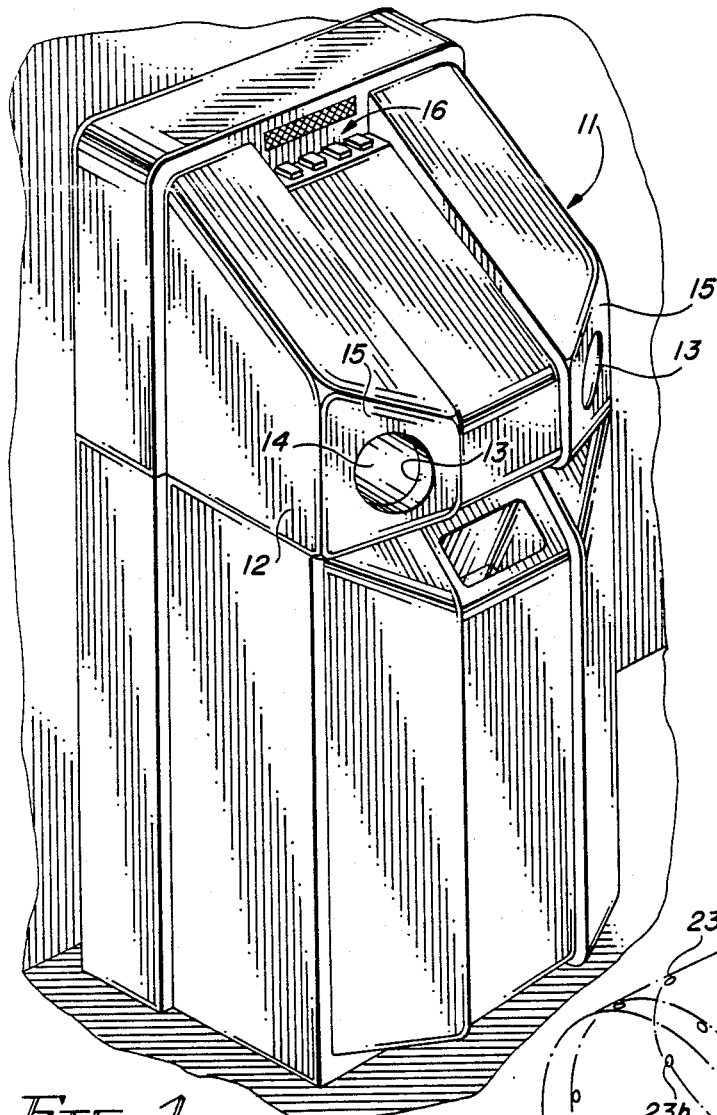
FIG. 1 is a three-quarter front perspective view from above of a hand and forearm cleansing unit of the type utilizing this invention.

In FIG. 1 reference numeral 11 designates generally a free standing hand and forearm cleansing unit the components of which are housed in a cabinet 12. Unit 11 is the type which can be installed in a hospital or any other location where employees or occupants are required to periodically cleanse their hands.

The cabinet 12 for unit 11 has a pair of openings 13 in the front thereof through which the hands and forearms of a user can be inserted into cleansing chambers 14 inside the cabinet Openings 13 are spaced apart a distance which is approximately the same as the distance between the elbows of a user standing before the unit and holding his hands and forearms outstretched before him. Openings 13 are also preferably positioned in surface areas 15 of the cabinet 12 which are angled back from the face of the cabinet so that the two areas 15 are at an obtuse angle with respect to each other. The result of this arrangement is that the axes of the openings 13 are at an acute angle with respect to each other to comfortably permit the entry of the hands and forearms of the user to the interior of cabinet 12.

Cabinet 12 also has on the exterior thereof, a control center 16 at which the user selects and programs the cleansing cycle he desires. For example, in addition to a conventional cleansing cycle in which a mixture of soap and water is used as a cleansing fluid and plain water is used as a rinse fluid, the apparatus may be programmed to subject the hands and forearms to a disinfecting treatment as well. Moreover, the apparatus may be constructed to permit the user to program the sequence and duration of the several steps.

This invention is concerned not with any particular type of cleansing or disinfecting fluids or their sequence of application, but rather with the apparatus for and method of application of the cleansing fluid to the hands and forearms of the user. To this end, the invention contemplates that the cleansing fluid be sprayed onto the hands and forearms from and within a pair of rotatable cylinders which provide therein the cleansing chambers 14 (See FIGS. 2 and 3).

Each cylinder 17 has an open, or forward, end 18 through which the hands and arms of the user can be inserted into the cleansing chamber 14 therein. Each cylinder 17 also preferably has its opposite, or rear, end 19 closed by a frusto-concical end closure 20.

Disposed about the inner surface of each cylinder 17 are a plurality of spray nozzles which are adapted to spray cleansing fluid inwardly into the cleansing chamber onto the hands and forearms of the user. According to this invention, there are at least three different sets of spray nozzles in each cylinder 17 and each nozzle set has a slightly different function.

In the first nozzle set the nozzles are identified by reference numeral 21 and function to spray cleansing fluid onto the hands and fingers of the user. These nozzles 21 are preferably positioned on the frusto-conical end closure 20 of each cylinder. Nozzles 21 are arranged to spray cleansing fluid radially inwardly of the chamber 14, and somewhat toward the open end 18 of the cylinder 17. There are a plurality of nozzles 21 disposed around the inner surface of the end closure 20 to insure that all areas of the fingers and particularly the fingernails are subjected to sprays of cleansing fluid. Rotation of cylinder 17 assures coverage of all areas of the fingers and hands with a cleansing fluid spray.

Each cylinder also preferably possesses a second set of spray nozzles which are identified by reference numeral 22. Nozzles 22 are arranged in a ring on the inner surface of each cylinder 17 just inside the open end 18 of the cylinder. Nozzles 22 are arranged to spray cleansing fluid radially inwardly of the cleansing chamber 14 and slightly toward the rear end 19 of the chamber. The set of nozzles 22 serves as a curtain to inhibit the splashing of cleansing fluid outside the cleansing chamber 14. Of course, cleansing fluid sprayed by nozzles 22 impacts on the forearm of the user and supplements the cleansing action of other sprays in the chamber 14.

The last of the preferred three sets of nozzles comprises nozzles 23 positioned on the inner surface of each cylinder 17 and extending in a helical array along the cylinder. The disposition of nozzles 23 can best be appreciated by reference to both FIG. 3 and the schematic illustration in FIG. 4. There are eight nozzles 23 in the third set of nozzles and they have been designated 23a through 23h as they are consecutively arranged in a helical path along the inner surface of each cylinder 17.

Figure 4:
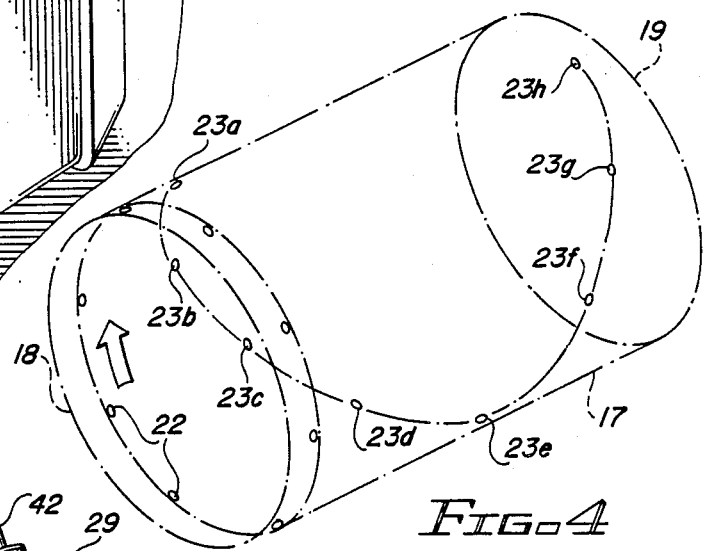
FIG. 4 is a schematic illustration of one of the cylinders and certain of the cleansing fluid spray nozzles thereto.

The disposition of the helical set of nozzles 23a–h is preferably coordinated with the direction of rotation of each cylinder 17 (See arrow in FIG. 4), so that the forearm and the heel portion of the hand are swept by a succession of sprays traveling from the elbow region of the forearm toward the hand. It will be noted that the direction of rotation of cylinders 17 in FIG. 4, is clockwise when viewed from the open end 18 of the cylinder The nozzles 23a–h are arranged in a left-hand helical pattern, or array, extending from the open end 18 to the closed end 19 of the cylinder. With this correlation between cylinder rotation and the disposition of nozzles 23a–h each longitudinal strip of skin surface on the forearm will be swept by a succession of sprays moving from the elbow region to the hand region.

Subjecting the skin surface of the hands and forearms of the user to moving sprays of cleansing fluid produces a cleansing effect much like the "trampoline" effect produced by the pulsating jet sprays of prior apparatus. However, the moving sprays of this invention can be produced by merely rotating cylinders 17 and the sets of nozzles 21, 22, and 23 carried therein. Considerably less effort and energy are required to rotate cylinders 17 than to produce pulsating or varying pressure cleansing fluid jets. Thus, the apparatus of this invention can produce equal or better cleansing with the expenditure of less energy and with less heavy and bulky motors and other equipment than was required with prior apparatus.

Spent cleansing fluid falling free of the hands and the forearms of the user exits the two cleansing chambers through drain openings 24 in the sidewalls of the cylinders 17 near the rear end 19 of each cylinder.

To facilitate the draining of the cleansing fluid from the cylinder 17 these cylinders are preferably mounted with their axes at a slight angle to the horizontal, for example, approximately 10 degrees (See FIG. 3). With the open end 18 of each cylinder 17 positioned higher than the rear end 19 thereof the cleansing fluid flows by gravity toward the drain openings 24 Of course, the frusto-conical configuration of end closures 20 of each cylinder also promotes the flow of cleansing fluid to the drain openings 24.

The slight downward tilt to the cleansing chambers 14 occasioned by mounting cylinder 17 at an angle to the horizontal, can be easily and comfortably accommodated by the hands and forearms The hands and forearms can comfortably be tilted downwardly by this slight angle, particularly when the hands are closer together than the elbows as is dictated by the acute angle between the axes of the cleansing chambers 14, as mentioned previously.

Figure 2:
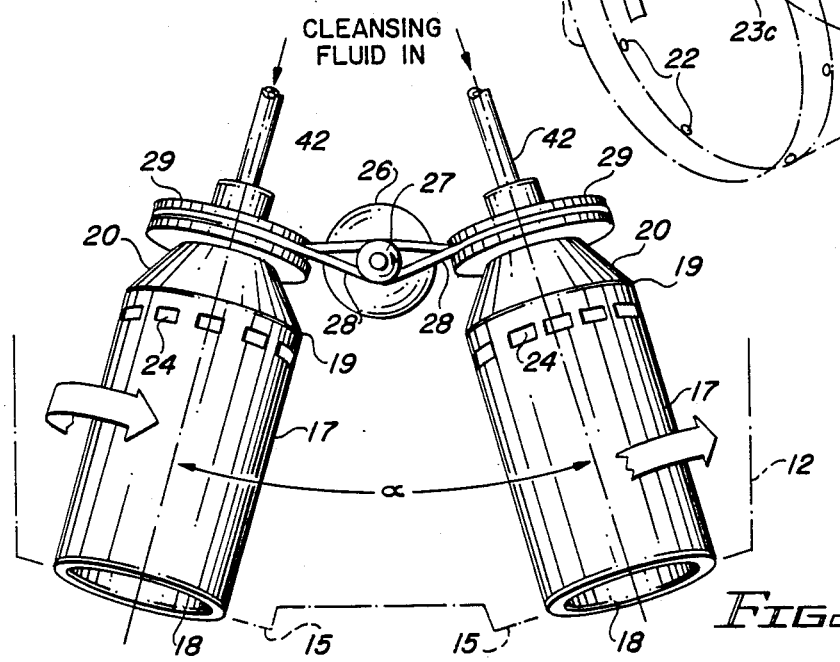
FIG. 2 is a diagrammatic plan illustration of a pair of rotatable cylinders employed in the invention.

The preferred relative positioning of rotatable cylinders 17 and the drive mechanism therefore, are diagrammatically illustrated in FIG. 2. It is to be noted that the axes of the cylinders 17 are disposed at an angle to each other with the open ends 18 of the cylinders being further apart than the closed ends 19 thereof. The angle of the displacement, indicated by the letter $\alpha$, is from approximately 20 degrees to approximately 40 degrees and preferably approximately 30 degrees. This represents the comfortable disposition of the persons forearms when they are held out in the front of the body slightly above waist high and assures that a person using the cleansing unit feels comfortable in doing so. It can be readily appreciated that any discomfort experienced by the user would discourage further use of the cleansing unit and is, therefore, studiously to be avoided.

The drive system diagrammatically illustrated in FIG. 2 comprises an electric motor 26 having a pulley 27 thereon for driving a pair of belts 28 which are looped respectively around pulleys 29 carried at the ends of cylinders 17.

More details of the construction and mounting of each cylinder 17 are illustrated in FIGS. 3 and 5. Each cylinder 17 is preferably formed of an inner liner 31 and an outer liner 32. Liners 31 and 32 are joined in sealing engagement at 33 near the open end 18 of the cylinder. Liners 31 and 32 are also sealed together around each drain opening 24 as indicated at 34. Elsewhere throughout liners 31 and 32, including the closure region 20 of the cylinder 17, the liners are radially spaced apart to provide a flow passage 36 through which cleansing fluid can be conveyed to nozzles 21 and 22 and 23. Liners 31 and 32 can be mechanically joined by means of screws 37 passing through complementary end wall regions of the liner.

Nozzles 21, 22 and 23 can be conveniently provided by drilling or casting in place openings in the inner liner 31 at appropriate locations. Nozzles 21, 22 and 23 can, of course, be provided by other means, such as threaded inserts (not shown) carried by the inner liner 31. The important consideration so far as nozzles 21, 22 and 23 are concerned is that, whatever mechanism is used to create the various sprays, that mechanism must not present any significant protruberance on the inner surface of the cylinder 17. That surface must be generally smooth so that it presents no hazard or discomfort for the hands and forearms of the user when the cylinders are rotating. Nozzle formed merely by drilling or casting in place openings in the inner are ideal in this respect because they present no protruberances inside the cylinder 17 and, therefore, present no hazard to the user.

There are advantages to providing the inner liner 31 of each cylinder 17 with gentle corrugations, or undulations, as shown in FIG. 3. In the first place, such corrugations stiffen and strengthen the inner liner 31 and, in turn, impart rigidity and strength to the cylinder 17.

Further advantages are achieved if the corrugations in liner 31 are made up of short sections 38 extending inwardly and rearwardly in the cylinder 17 and relatively longer sections 39 joining the short sections and extending outwardly and rearwardly in the cylinder. The longer outwardly and rearwardly sloping sections 39 constitute the major portion of the inner surface area of the cylinder and tend to direct the spray splashing against the inner surface of the cylinder 17 rearwardly toward the drain openings 24 and away from the open end 18 of the cylinder This has the effect of reducing the tendency for cleansing fluid to splash out through opening 13 in the front of the cabinet.

Some prior art cleansing units have resorted to the use of elastic boots to seal the front openings to the cleansing chambers to prevent outsplashing of cleansing fluid. Such arrangements are not satisfactory in sterile environments because the boots contact the forearms and hands as they are removed from the cleansing chamber and may contaminate the cleansed hands and forearms.

A further advantage to the short and long corrugation sections 38 and 39 in liner 31 lies in the longer sections 39 providing convenient locations for the nozzles 22 and 23. With nozzles 22 and 23 located on the sloping longer sections 39 the sprays therefrom (as shown by the dotted lines in FIG. 3), are directed slightly rearwardly in the cleansing chamber 14. This further reduces outsplashing of cleansing fluid from the cabinet opening 13.

It is to be noted that the inner and outer liners 31 and 32, of each cylinder 17 can be made to be closely spaced so as to reduce the volume of flow passage 36 to a minimum. This can be important in a cleansing unit using warm water, as most cleansing units do, because at it reduces the quantity of cleansing fluid retained in the cylinders from a previous cleansing operation. That leftover fluid often will have cooled to room temperature and must be purged before an effective cleansing cycle can be commenced.

With the cylinder 17 being made up of inner and outer spaced liners 31 and 32 to provide, in effect, an open cylindrical flow passage 36 there is another phenomenon that should be dealt with. As each cylinder 17 is rotated, the body of cleansing fluid in flow passage 36 tends to lag behind so there is relative circumferential motion generated between the cylinder 17 and the fluid therein. This motion can adversely affect the performance of nozzles 22 and 23. This adversity can be overcome by providing longitudinally extending dams 41 alongside each nozzle 22 and 23 on the outer surface of inner liner 31 (See FIG. 5). These dams 41 are disposed in the corrugations adjacent each nozzle 22 and 23 and lag behind their respective nozzles so far as the direction of rotation of the cylinder 17 is concerned. In this position the dams 41 block and impede rotational movement of cleansing fluid in flow passage 36 in the vicinity of each of the nozzles 22 and 23. Some of the kinetic energy in the fluid flowing in the vicinity of a nozzle 22 or 23 is converted by the dam 41 to static energy which improves the flow of cleansing fluid into and through the nozzle thereby increasing the latter's effectiveness in producing a forceful cleaning spray.

Figure 6:
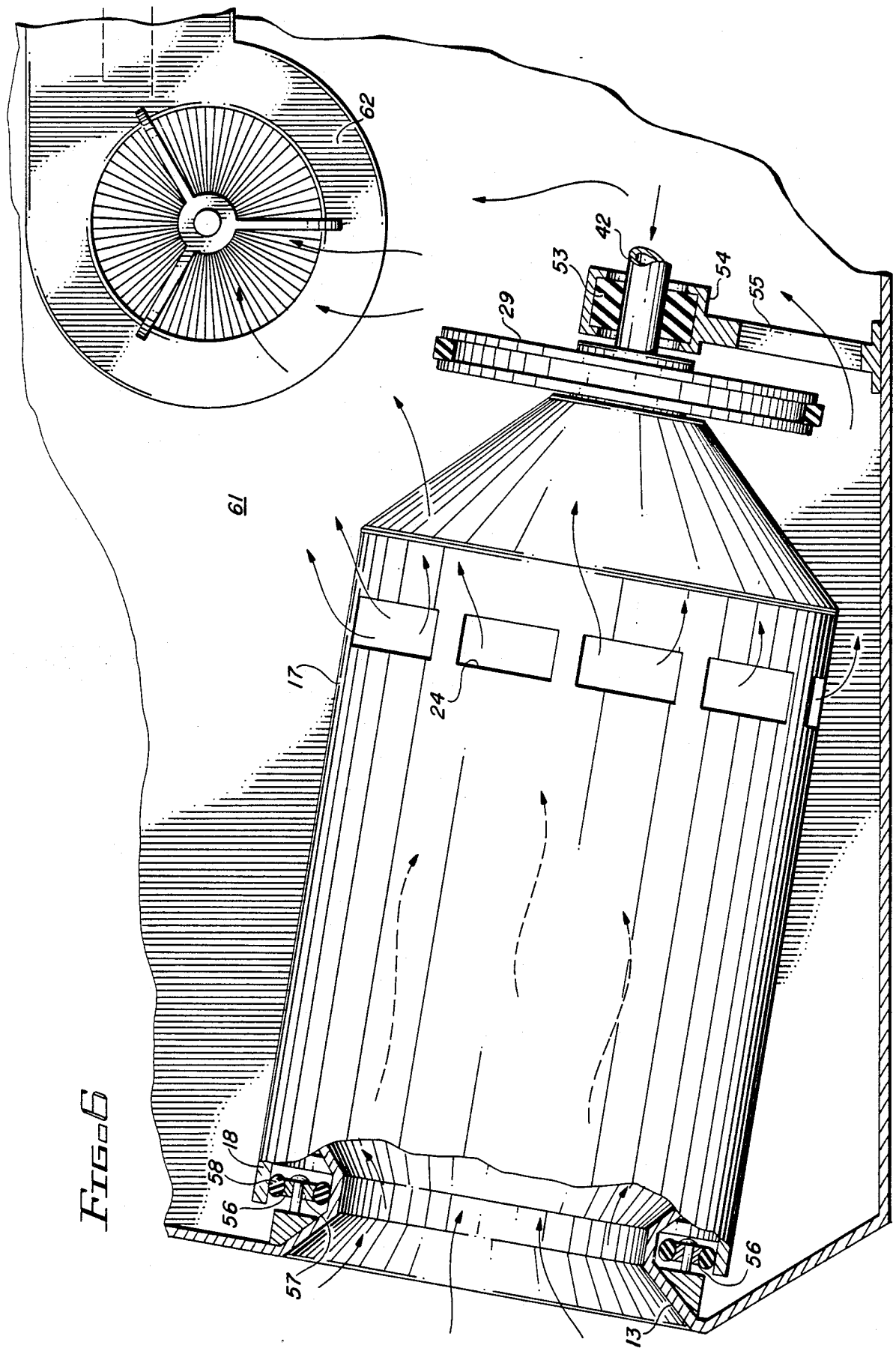
FIG. 6 is a fragmentary elevational view of the interior of a modified hand and forearm cleansing unit.

Means must be provided, of course, for supplying cleansing fluid to the flow passage 36 in each cylinder 17. In accordance with this invention this supply means is provided in conjunction with means for rotatably mounting each cylinder 17 within the unit cabinet 12. FIGS. 3 and 6 illustrate alternative mounting and fluid supply means.

Referring first to the mode illustrated in FIG. 3, cleansing fluid is supplied to the cylinder 17 by means of a stationary supply conduit 42. Conduit 42 has a rear end portion thereof attached to a bracket 43 by adjustable clamping means 44. This portion of conduit 42 is also connected to a source of cleansing fluid (not shown). The opposite end of conduit 42 is in open communication with flow passage 36 between cylinder inner and outer liners 31 and 32.

Outer liner 32 is preferably provided with a tubular extension 46 by which the cylinder 17 is rotatably mounted on conduit 42. Tubular extension 46 comprises a sealing section 47 which closely confines an elastomeric seal 48 between the extension and conduit 42. Seal 48 prevents the escape of washing fluid from cylinder 17 along the outer surface of supply conduit 42. Rotational support for the cylinder 17 is provided by a somewhat larger diameter bearing section 49 of extension 46 which houses bearings 51 between section 49 and conduit 42. Bearing section 49 of extension 46 also carries a pulley 29 by which rotational movement is imparted to cylinder 17.

The forward, or open, end 18 of each cylinder 17 is preferably supported by a plurality of rollers 52 engaging the inner surface of the cylinder.

FIG. 6 illustrates another mounting mode for the cylinder 17. The rear end of cylinder 17 is rotatably carried the stationary supply conduit 42. The coupling system between these components can be the same as illustrated in FIG. 3 and described above. The conduit 42, however, is mounted in an elastomeric sleeve 53 of rubber or rubber-like material which is, in turn, carried in a mounting sleeve 54 atop a bracket 55.

The forward, or open, end 18 of each cylinder 17 is supported by a plurality of elastomeric rollers 56. These rollers are preferably made from metalic inner sleeves 57 having tires 58 mounted thereon. The tires 58 are made from rubber or other elastomeric material. The advantage of the elastomeric mounting system illustrated in FIG. 6 is that it assures positive and reliable rotational support for cylinder 17 even though manufacturing tolerances allow some misalignment or displacement of mounting bracket 55 and rollers 56.

The invention mode illustrated in FIG. 6 has one further advantageous feature associated therewith. This apparatus is equipped with means for further reducing the out splashing of cleansing fluid through the cabinet access openings 13. Both cylinders 17 (only one is shown in FIG. 6) are contained within a chamber 61 which also has a motor driven blower 62 associated therewith. Blower 62 is adapted to expel air from chamber 61. In so doing, air is drawn into chamber 61 through the open ends 18 of cylinders 17, through the cleansing chambers therein and out of the cleansing chambers through drain openings 24 into chamber 61. This flow of air into cylinders 17 inhibits the cleansing fluid spray from exiting cabinet openings 13 through the open ends of the cylinders and keeps the spray confined within the cleansing chambers 14.

From the foregoing it should be apparent that this invention provides apparatus for effectively cleansing the hands and forearms of the user. The apparatus has a number of features which contribute to its effectiveness while permitting the apparatus to be manufactured and operated at costs which are comparable to or less than prior apparatus intended for similar purposes.

What is claimed is:

1. In hand and forearm cleansing apparatus, a cylinder having an inner surface forming a cleaning chamber, said cylinder being rotatable about its axis and having an open end through which the hand and forearm of the user enters the cleansing chamber, nozzle means in the wall of said cylinder, said nozzle means presenting no significant protruberances on the inner surface of the cylinder, means for conveying cleansing fluid to said nozzle means, and means for rotating said cylinder.

2. The apparatus of claim 1 wherein said nozzle means comprises a series of nozzles disposed in a helical array in the cylinder wall.

3. The apparatus of claim 2 wherein the disposition of the helical array of nozzles and the direction of rotation of the cylinder is such that each longitudinal strip of forearm surface is subjected to a series of sprays of cleansing fluid from said nozzle means commencing near said open end of the cylinder and progressing toward the hand.

4. The apparatus of claim 1 wherein the inner surface of the cylinder has smooth corrugations therein, and said nozzle means comprises a plurality of nozzles positioned on the corrugations to direct water inwardly of the cylinder and away from said open end of the cylinder.

5. The apparatus of claim 1 further characterized in that the axis of said cylinder is at an angle to the horizontal with the open end elevated with respect to the opposite end and means for draining fluid from the region of the opposite end of the cylinder.

6. The apparatus of claim 5 further including blower means for drawing air into the open end of said cylinder through said cleansing chamber and through said draining means.

7. The apparatus of claim 6 further comprising a chamber containing said cylinder, and said blower means is adapted to evacuate air from said chamber to draw air into the open end of the cylinder through said cleansing chamber and through said draining means.

8. The apparatus of claim 5 further comprising a stationary cleansing fluid conduit forming a part of said fluid conveying means, said cylinder being rotatably mounted on said conduit at said opposite end.

9. The apparatus of claim 8 wherein said cylinder is supported by an elastomeric mounting for said cleansing fluid conduit and a plurality of elastomeric rollers engaging the cylinder in the vicinity of its open end.

10. The apparatus of claim 1 further characterized in that the cylinder is comprised of an outer liner and an inner liner, said liners having a space there between to permit cleansing fluid to pass therethrough to said nozzle means.

11. The apparatus of claim 10 further comprising dam means disposed in said space in the vicinity of said nozzle 12. The apparatus of claim 10 wherein said nozzle means. means are position entirely in said inner liner.

13. The apparatus of claim 12 wherein said inner liner is corrugated.

14. The apparatus of claim 10 further comprising a stationary cleansing fluid conduit communicating with the space between said liners and said cylinder is rotatably mounted on said conduit at the end thereof opposite said open end.

15. The apparatus of claim 1 further comprising blower means for drawing air into said chamber through the open end of said cylinder.

16. The apparatus of claim 15 further comprising a chamber containing said cylinder, and said blower means is adapted to evacuate air from said chamber to draw air into the open end of the cylinder.

17. The apparatus of claim 11 further comprising a stationary cleansing fluid conduit forming a part of said fluid conveying means, said cylinder being rotatably mounted on said conduit at the end thereof opposite said open end.

18. The apparatus of claim 17 wherein said cylinder is supported by an elastomeric mounting for said cleansing fluid conduit and a plurality of elastomeric rollers engaging the cylinder in the vicinity of its open end.

19. In hand and forearm cleansing apparatus, a pair of cylinders having inner surfaces forming cleansing chambers, said cylinders being rotatable about their axes and each having an open end through which a hand and forearm of a user enters the cleansing chamber therein, the axes of said cylinders being displaced from each other at an angle to comfortably receive the hands and forearms of a user, nozzle means in the walls of said cylinders, said nozzle means presenting no significant protruberances on the inner surface of either cylinder, means for conveying cleansing fluid to said nozzle means, and means for rotating said cylinders.

20. The apparatus of claim 19 wherein the said angle of displacement is from approximately 20 degrees to approximately 40 degrees.

21. The apparatus of claim 19 wherein the axes of said cylinders are also displaced at an angle to the horizontal.

22. The apparatus of claim 21 wherein the angle of displacement from the horizontal is approximately 10 degrees.

* * * * *